United States Patent
Grady et al.

(10) Patent No.: US 9,514,530 B2
(45) Date of Patent: Dec. 6, 2016

(54) SYSTEMS AND METHODS FOR IMAGE-BASED OBJECT MODELING USING MULTIPLE IMAGE ACQUISITIONS OR RECONSTRUCTIONS

(71) Applicant: HeartFlow, Inc., Redwood City, CA (US)

(72) Inventors: Leo Grady, Millbrae, CA (US); Michiel Schaap, Mountain View, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 14/254,519

(22) Filed: Apr. 16, 2014

(65) Prior Publication Data
US 2015/0302578 A1   Oct. 22, 2015

(51) Int. Cl.
*G06K 9/00* (2006.01)
*G06T 7/00* (2006.01)
(Continued)

(52) U.S. Cl.
CPC .............. *G06T 7/0012* (2013.01); *A61B 5/489* (2013.01); *A61B 6/032* (2013.01); *A61B 6/503* (2013.01); *A61B 6/504* (2013.01); *A61B 6/5247* (2013.01); *A61B 8/00* (2013.01); *G06F 19/321* (2013.01); *G06F 19/3437* (2013.01); *G06K 9/6202* (2013.01); *G06T 7/0014* (2013.01); *G06T 11/008* (2013.01); *G06T 17/00* (2013.01); *A61B 5/0066* (2013.01); *A61B 5/055* (2013.01);
(Continued)

(58) Field of Classification Search
None
See application file for complete search history.

(56) References Cited

U.S. PATENT DOCUMENTS 8,285,011 B2 * 10/2012 Chen et al. ................... 382/128
8,315,812 B2    11/2012 Taylor
(Continued)

OTHER PUBLICATIONS

Schuurbiers, Johan C.H. et al. "In Vivo Validation of CAAS QCA-3D Coronary Reconstruction Using Fusion of Angiography and Intravascular Ultrasound (ANGUS)", Catheterization and Cardiovascular Interventions, vol. 73, Issue 5, Oct. 27, 2008, 8 pages.*
(Continued)

*Primary Examiner* — Sumati Lefkowitz
*Assistant Examiner* — Ryan P Potts
(74) *Attorney, Agent, or Firm* — Bookoff McAndrews, PLLC

(57) ABSTRACT

Systems and methods that involve integrating imaging data from multiple sources to create a single, accurate model of a patient's anatomy. One method includes receiving a representation of a target object for modeling; determining one or more first anatomical parameters of the target anatomical object from at least one of one or more first images of the target anatomical object; determining one or more second anatomical parameters of the target anatomical object from at least one of one or more second images of the target anatomical object; updating the one or more first anatomical parameters based at least on the one or more second anatomical parameters; and generating a model of the target anatomical object based on the updated first anatomical parameters.

21 Claims, 10 Drawing Sheets

(51) Int. Cl.
  *G06K 9/62* (2006.01)
  *G06F 19/00* (2011.01)
  *G06T 17/00* (2006.01)
  *A61B 6/03* (2006.01)
  *A61B 6/00* (2006.01)
  *A61B 8/00* (2006.01)
  *G06T 11/00* (2006.01)
  *A61B 5/055* (2006.01)
  *A61B 5/00* (2006.01)
  *G01R 33/56* (2006.01)

(52) U.S. Cl.
  CPC ......... *A61B 6/5205* (2013.01); *A61B 2576/02* (2013.01); *G01R 33/5608* (2013.01); *G06T 2210/41* (2013.01)

(56) References Cited

U.S. PATENT DOCUMENTS

| | | | |
|---|---|---|---|
| 8,406,851 | B2 | 3/2013 | West et al. |
| 8,761,474 | B2 | 6/2014 | Yu et al. |
| 9,058,692 | B1 | 6/2015 | Grady et al. |
| 2003/0028101 | A1 | 2/2003 | Weisskoff et al. |
| 2006/0036167 | A1* | 2/2006 | Shina ............ 600/433 |
| 2007/0019846 | A1 | 1/2007 | Bullitt et al. |
| 2008/0205722 | A1 | 8/2008 | Schaefer et al. |
| 2008/0247622 | A1 | 10/2008 | Aylward et al. |
| 2009/0154785 | A1 | 6/2009 | Lynch et al. |
| 2010/0135529 | A1 | 6/2010 | Li et al. |
| 2011/0064290 | A1 | 3/2011 | Punithakumar et al. |
| 2011/0150312 | A1 | 6/2011 | Takanami et al. |
| 2012/0201442 | A1 | 8/2012 | Beck et al. |
| 2013/0077872 | A1 | 3/2013 | Kitamura et al. |
| 2013/0129174 | A1* | 5/2013 | Grbic ............ G06T 7/0012 382/131 |
| 2013/0322723 | A1 | 12/2013 | Akhbardeh et al. |
| 2014/0022253 | A1* | 1/2014 | Nakagawa ............ G06T 7/0032 345/427 |
| 2014/0064591 | A1 | 3/2014 | Sasaki et al. |
| 2014/0119628 | A1 | 5/2014 | Elad at al. |
| 2014/0200867 | A1 | 7/2014 | Lavi et al. |
| 2015/0302631 | A1 | 10/2015 | Grady et al. |

OTHER PUBLICATIONS

Yang, Guanyu et al., "Automatic centerline extraction of coronary arteries in coronary computed tomographic angiography," Int J Cardiovasc Imaging, Jun. 3, 2011, 13 pages.*

Boogers, Mark J. et al., "Automated quantification of coronary plaque with computed tomography: comparison with intravascular ultrasound using a dedicated registration algorithm for fusion-based quantification," European Heart Journal 33, 2012, 10 pages.*

Prause, Guido P. M. et al., "Semi-automated segmentation and 3-D reconstruction of coronary trees: Biplane angiography and intravascular ultrasound data fusion,"Physiology and Function from Multidimensional Medical Imaging 1996, Apr. 8, 1996, 12 pages.*

U.S. Appl. No. 14/254,491, filed Apr. 16, 2014, Leo Grady et al.; "Systems and Methods for Image-Based Object Modeling using Multiple Image Acquisitions or Reconstructions".

International Search Report and Written Opinion mailed on Jul. 20, 2015, in corresponding International PCT Application No. PCT/US2015/025691, filed on Apr. 14, 2015.

Beck et al., "Statistical Modeling of the Arterial Vascular Tree", 2011, pp. 1-6, vol. 7962, Proc. of SPIE.

Nakamura et al., "Segmentation of Brian Magnetic Resonance Images for Measurement of Gray Matter Atrophy in Multiple Sclerosis Patients", Feb. 1, 2009, pp. 769-776, vol. 44, No. 3, Neuroimage.

Gao, Weichen, "Development of Human Lung Query Atlas", Master of Science Thesis, Dec. 2010, pp. 1-117, University of Iowa.

Florez et al. (NPL: "3D Models for Vascular Lumen Segmentation in MRA images and for artery-stenting simulation", Published ScienceDirect.com, Mar. 28, 2013).

* cited by examiner

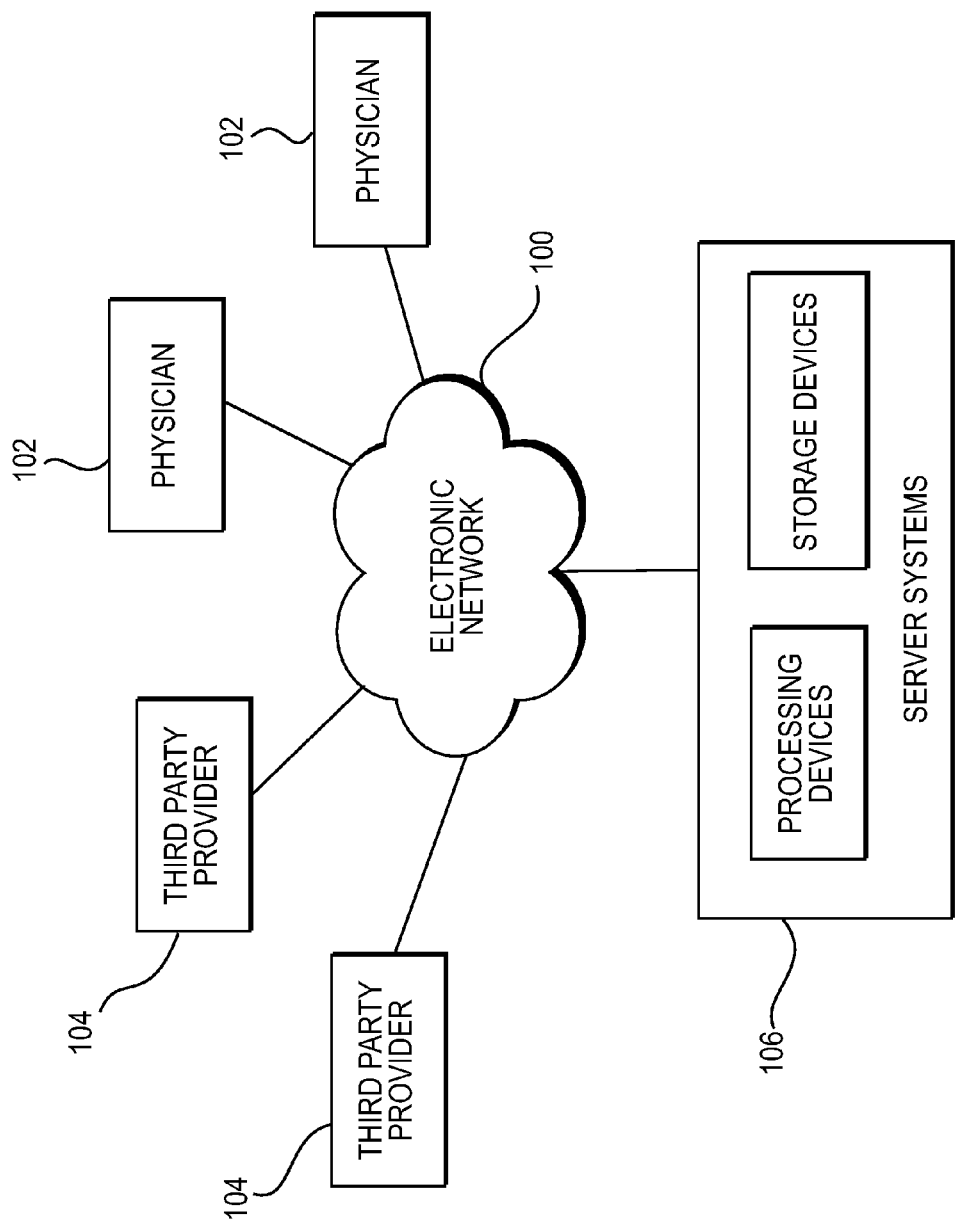

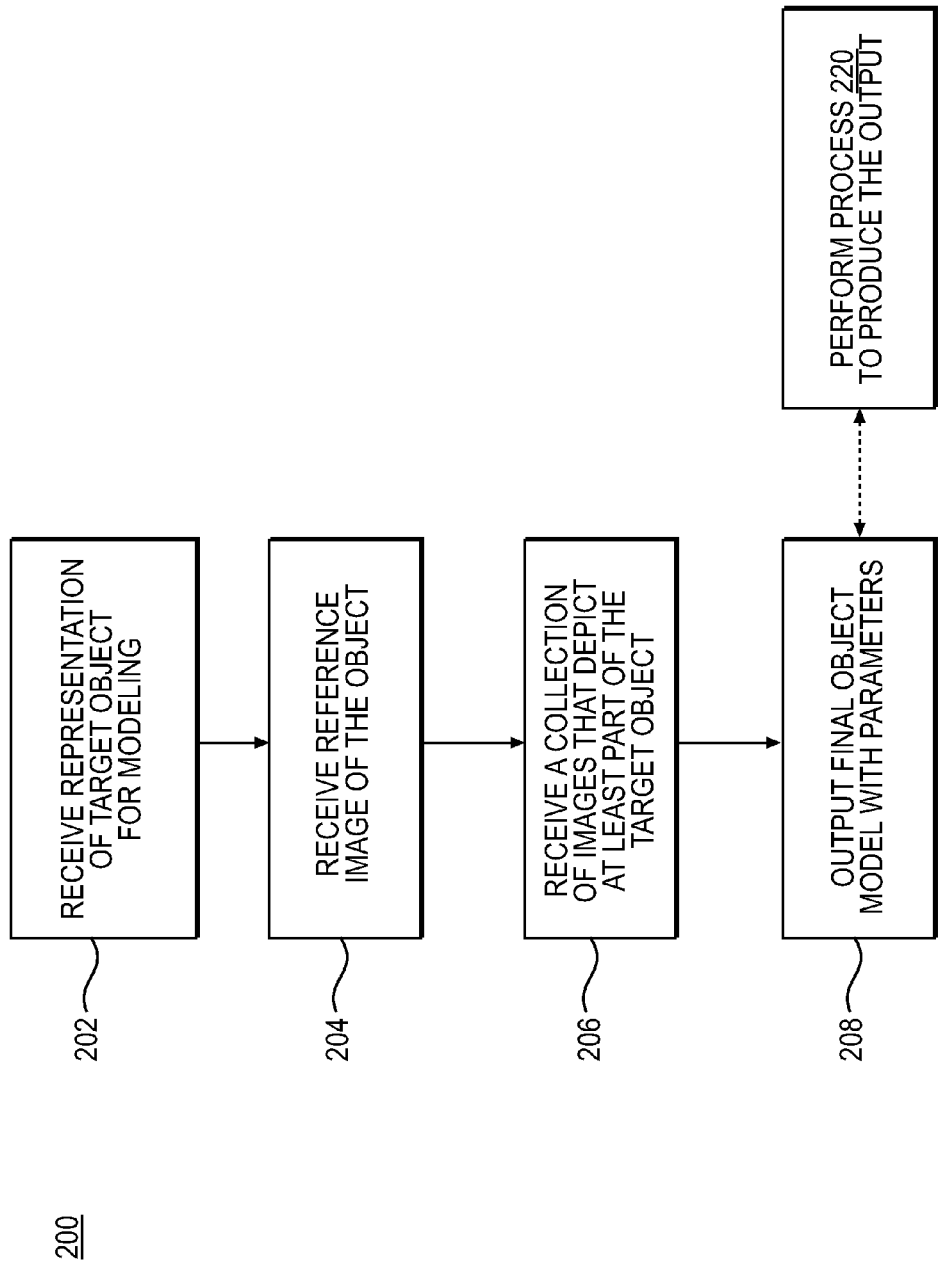

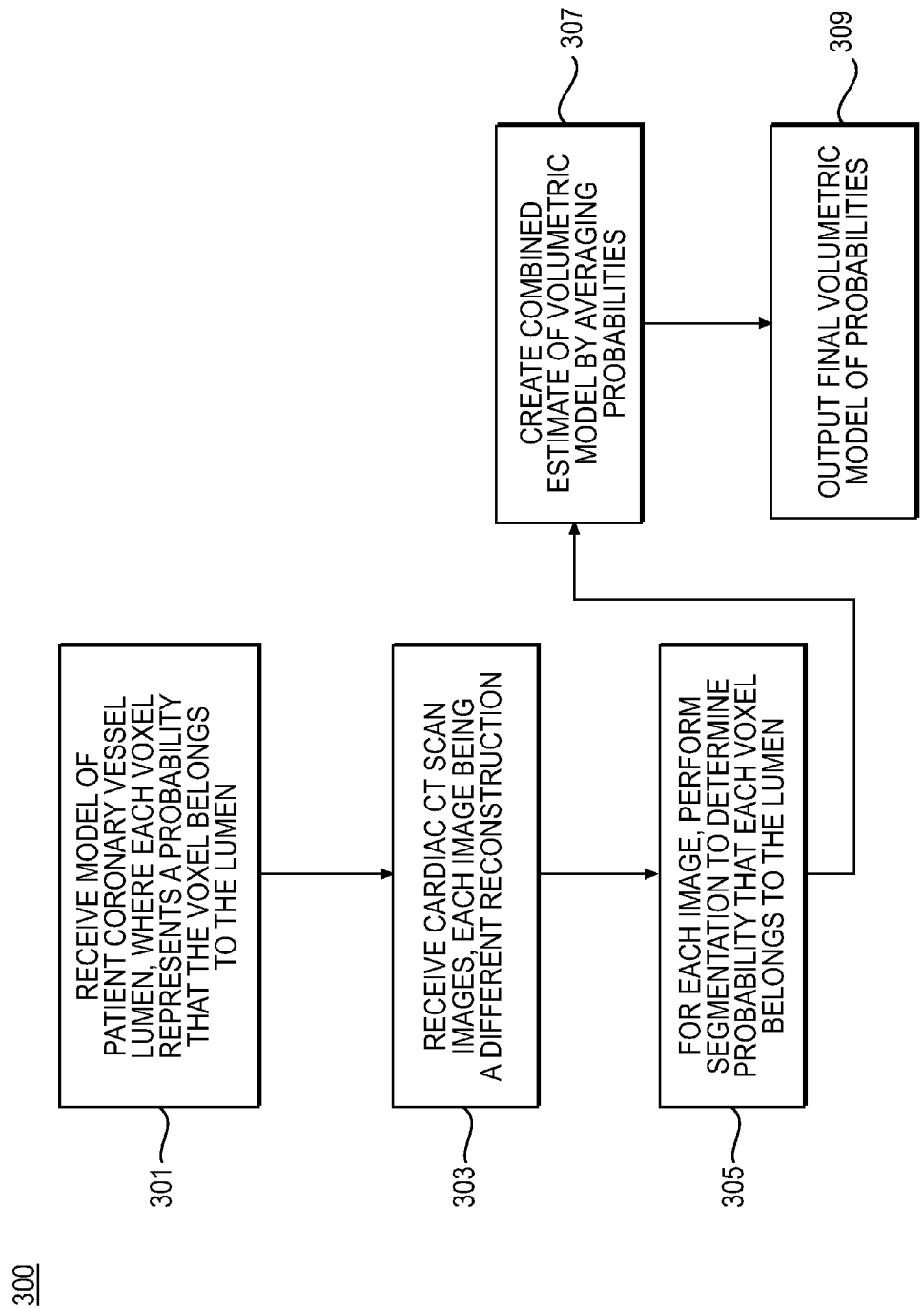

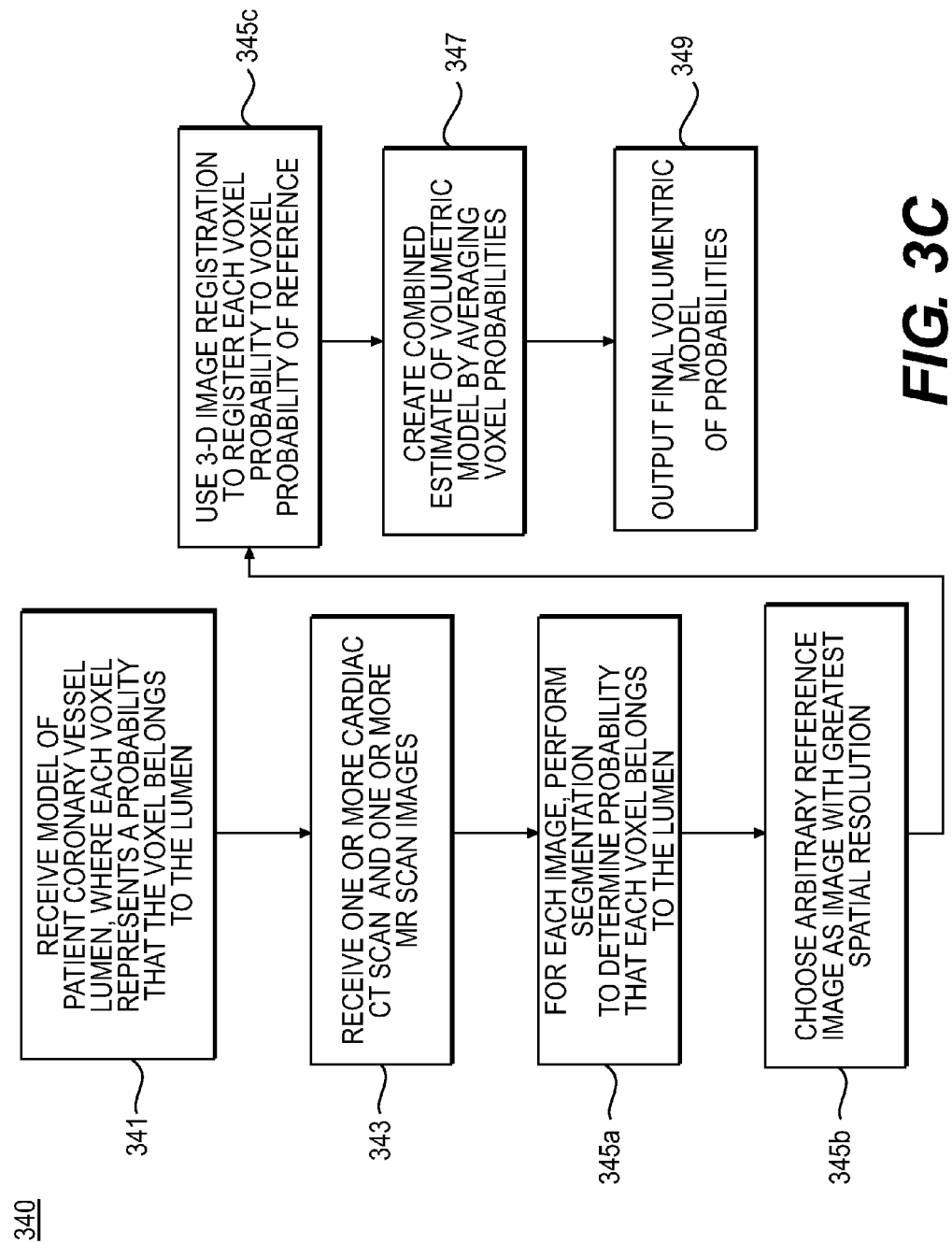

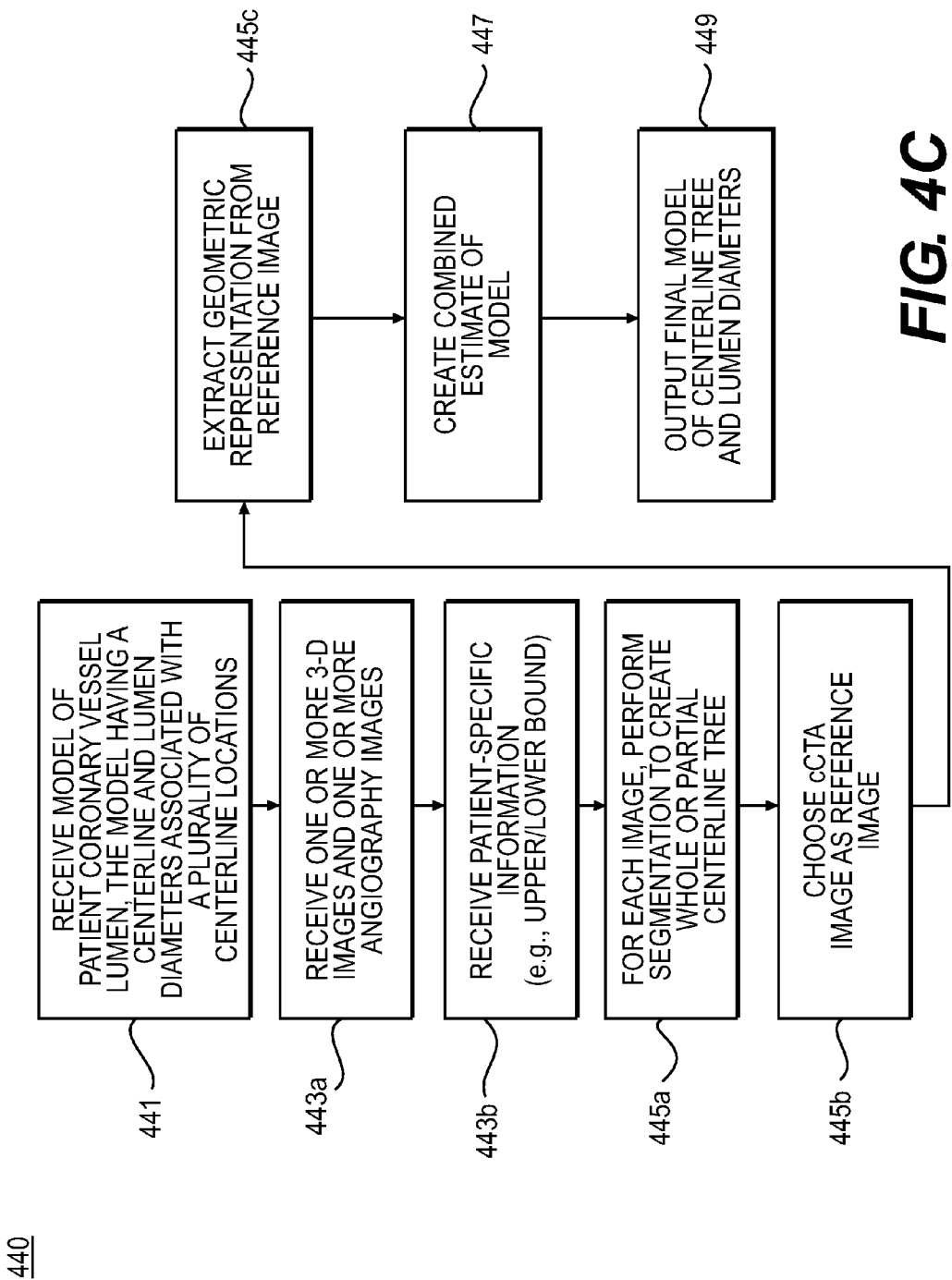

SYSTEMS AND METHODS FOR IMAGE-BASED OBJECT MODELING USING MULTIPLE IMAGE ACQUISITIONS OR RECONSTRUCTIONS

FIELD OF THE INVENTION

Various embodiments of the present disclosure relate generally to medical imaging and related methods. More specifically, particular embodiments of the present disclosure relate to systems and methods for image-based object modeling using multiple image acquisitions or reconstructions.

BACKGROUND

Medical imaging and extraction of anatomy from imaging is important, as evidenced by the many means of medical imaging available. Common forms of medical imaging include computed tomography (CT) scans, magnetic resonance imaging, intravascular ultrasound, intravascular optical coherence tomography, angiography, and histopathology optical images. CT scans are x-ray images of "slices" of a scanned object. For example, CT scans are commonly images taken as cross-sectional slices, perpendicular to the long axis of the body. Cardiac CT scans may include calcium-score screening and/or angiography. Calcium score screening scans may be used to detect calcium deposits in coronary arteries, contributing to predictions of heart problems. CT angiography is CT scanning including intravenous (IV) contrast dye to better show blood vessels and organs. Although also capable of producing tomographic images, magnetic resonance (MR) imaging uses magnetic field properties to create the images. Because CT and MRI images are produced differently, resultant images highlight different tissue properties. MR images offer better quality in soft tissue images than CT scans; CT scans image bone and blood vessels in addition to soft tissue, although the soft tissue detail is inferior to that of MR images. Depending on the anatomy of interest and purpose of imaging, CT and MR may be considered complimentary imaging techniques.

Intravascular ultrasound (IVUS) is a type of imaging that visualizes the inside of blood vessels. Whereas CT and MR methods involve images taken as slices of a patient body, IVUS images are achieved via a catheter traveling through an artery or vein. Thus, IVUS images may essentially show cross-sections of the artery or vein, from the center of a blood vessel, out through the vessel wall and whatever diseased portion may exist at the wall. Intravascular optical coherence tomography (OCT) is an optical analog of the ultrasound imaging of IVUS. IVUS and OCT are analogous imaging modalities, but OCT's use of light (in place of sound) offers higher resolution images than IVUS. Briefly discussed in the context of CT scans, angiography is an imaging technique that employs an injection of a contrast agent into the blood stream to better show vessels or vessel openings. While CT angiography may be preferable for coronary disease detection, MR angiography is a viable alternative. Histopathological optical imaging includes visualization of tissue on a microscopic level. Histopathological imaging can be used to identify tissue or detect for various biomarkers. One common prerequisite for the analysis of histopathological images is the localization of cells, tissue or other anatomical and cellular objects within the images.

Based on images from techniques described above, anatomical models may be extracted to measure one or more properties of a patient's anatomy (e.g., a tumor or cardiac volume) or to support biophysical simulation (e.g., fluid simulation, biomechanical simulation, electrophysiological simulation, etc.). In order to accurately measure anatomical properties or predict physiological phenomena via simulation, a very precise patient-specific model must be created of the target anatomy. Imaging and subsequent extraction of anatomical models of the heart, for example, is of special importance. For instance, such imaging and modeling may provide evaluation of coronary artery disease, such as when a patient is suffering from chest pain, and/or a more severe manifestation of disease, such as myocardial infarction, or heart attack.

Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers). For example, anatomic data may be obtained noninvasively using coronary computed tomographic angiography (CCTA). CCTA may be used for imaging of patients with chest pain and involves using CT technology to image the heart and the coronary arteries following an intravenous infusion of a contrast agent.

However, single images may be insufficient to create ideal models. The foregoing general description and the following detailed description are exemplary and explanatory only and are not restrictive of the disclosure.

SUMMARY

According to certain aspects of the present disclosure, systems and methods are disclosed for modeling at least a portion of a patient's anatomy. One method includes: receiving a representation of a target object for modeling; determining one or more first anatomical parameters of the target anatomical object from at least one of one or more first images of the target anatomical object; determining one or more second anatomical parameters of the target anatomical object from at least one of one or more second images of the target anatomical object; updating the one or more first anatomical parameters based at least on the one or more second anatomical parameters; and generating a model of the target anatomical object based on the updated first anatomical parameters.

In accordance with another embodiment, a system for modeling at least a portion of a patient's anatomy, comprises: a data storage device storing instructions for modeling based on patient-specific anatomic image data; and a processor configured to execute the instructions to perform a method including receiving a representation of a target object for modeling; determining one or more first anatomical parameters of the target anatomical object from at least one of one or more first images of the target anatomical object; determining one or more second anatomical parameters of the target anatomical object from at least one of one or more second images of the target anatomical object; updating the one or more first anatomical parameters based at least on the one or more second anatomical parameters; and generating a model of the target anatomical object based on the updated first anatomical parameters.

In accordance with yet another embodiment, a non-transitory computer readable medium for use on a computer system containing computer-executable programming instructions for modeling at least a portion of a patient's anatomy is provided. The method includes: receiving a representation of a target object for modeling; determining one or more first anatomical parameters of the target anatomical object from at least one of one or more first images of the target anatomical object; determining one or more second anatomical parameters of the target anatomical object from at least one of one or more second images of the target anatomical object; updating the one or more first anatomical parameters based at least on the one or more second anatomical parameters; and generating a model of the target anatomical object based on the updated first anatomical parameters.

Another method includes: obtaining an initial model of at least a portion of a patient's coronary vasculature; determining one or more first anatomical parameters of the portion of the patient's coronary vasculature from at least one of one or more first images of the portion of a patient's coronary vasculature; determining one or more second anatomical parameters of the portion of the patient's coronary vasculature from at least one of one or more second images of the patient's coronary vasculature; updating the one or more first anatomical parameters based at least on the one or more second anatomical parameters; and generating a final model of the patient's coronary vasculature based on the updated first anatomical parameters.

In accordance with another embodiment, a system for modeling at least a portion of a patient's anatomy, comprises: a data storage device storing instructions for modeling based on patient-specific anatomic image data; and a processor configured to execute the instructions to perform a method including: obtaining an initial model of at least a portion of a patient's coronary vasculature; determining one or more first anatomical parameters of the portion of the patient's coronary vasculature from at least one of one or more first images of the portion of a patient's coronary vasculature; determining one or more second anatomical parameters of the portion of the patient's coronary vasculature from at least one of one or more second images of the patient's coronary vasculature; updating the one or more first anatomical parameters with the one or more second anatomical parameters; and generating a final model of the patient's coronary vasculature based on the updated first anatomical parameters.

In accordance with yet another embodiment, a non-transitory computer readable medium for use on a computer system containing computer-executable programming instructions for modeling at least a portion of a patient's anatomy is provided. The method includes: obtaining an initial model of at least a portion of a patient's coronary vasculature; determining one or more first anatomical parameters of the portion of the patient's coronary vasculature from at least one of one or more first images of the portion of a patient's coronary vasculature; determining one or more second anatomical parameters of the portion of the patient's coronary vasculature from at least one of one or more second images of the patient's coronary vasculature; updating the one or more first anatomical parameters based on the one or more second anatomical parameters; and generating a final model of the patient's coronary vasculature based on the updated first anatomical parameters.

Yet another method includes: receiving an initial model of cell locations and diameters of human cells; acquiring at least two histopathology images of at least a portion of a patient's anatomy; performing localization of cells in each of the at least two histopathology images to identify cell center locations and diameters of cells in each image; creating a combined estimate of cell center locations and diameters of cells matched between each of the at least two histopathology images; and generating a final cells model of cell center locations and diameters based on the combined estimate.

In accordance with another embodiment, a system for modeling at least a portion of a patient's anatomy, comprises: a data storage device storing instructions for modeling based on patient-specific anatomic image data; and a processor configured to execute the instructions to perform a method including: receiving an initial model of cell locations and diameters of human cells; acquiring at least two histopathology images of at least a portion of a patient's anatomy; performing localization of cells in each of the at least two histopathology images to identify cell center locations and diameters of cells in each image; creating a combined estimate of cell center locations and diameters of cells matched between each of the at least two histopathology images; and generating a final cells model of cell center locations and diameters based on the combined estimate.

In accordance with yet another embodiment, a non-transitory computer readable medium for use on a computer system containing computer-executable programming instructions for modeling at least a portion of a patient's anatomy is provided. The method includes: receiving an initial model of cell locations and diameters of human cells; acquiring at least two histopathology images of at least a portion of a patient's anatomy; performing localization of cells in each of the at least two histopathology images to identify cell center locations and diameters of cells in each image; creating a combined estimate of cell center locations and diameters of cells matched between each of the at least two histopathology images; and generating a final cells model of cell center locations and diameters based on the combined estimate.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 1 is a block diagram of an exemplary system and network for generating models from multiple patient-specific anatomic images, according to an exemplary embodiment of the present disclosure.

FIG. 2A is a block diagram of an exemplary method for creating a patient-specific model from multiple images, according to an exemplary embodiment of the present disclosure.

FIGS. 3A-3C are block diagrams of exemplary methods for coronary vessel modeling, where a final volumetric model includes probabilities that each voxel belongs to patient coronary vessel lumen, according to an exemplary embodiment of the present disclosure.

FIGS. 4A-4C are block diagrams of exemplary methods for coronary vessel modeling, where the final model is an object model of the centerline tree and lumen diameters of the coronary vessel, according to an exemplary embodiment of the present disclosure.

DESCRIPTION OF THE EMBODIMENTS

Figure 2B:
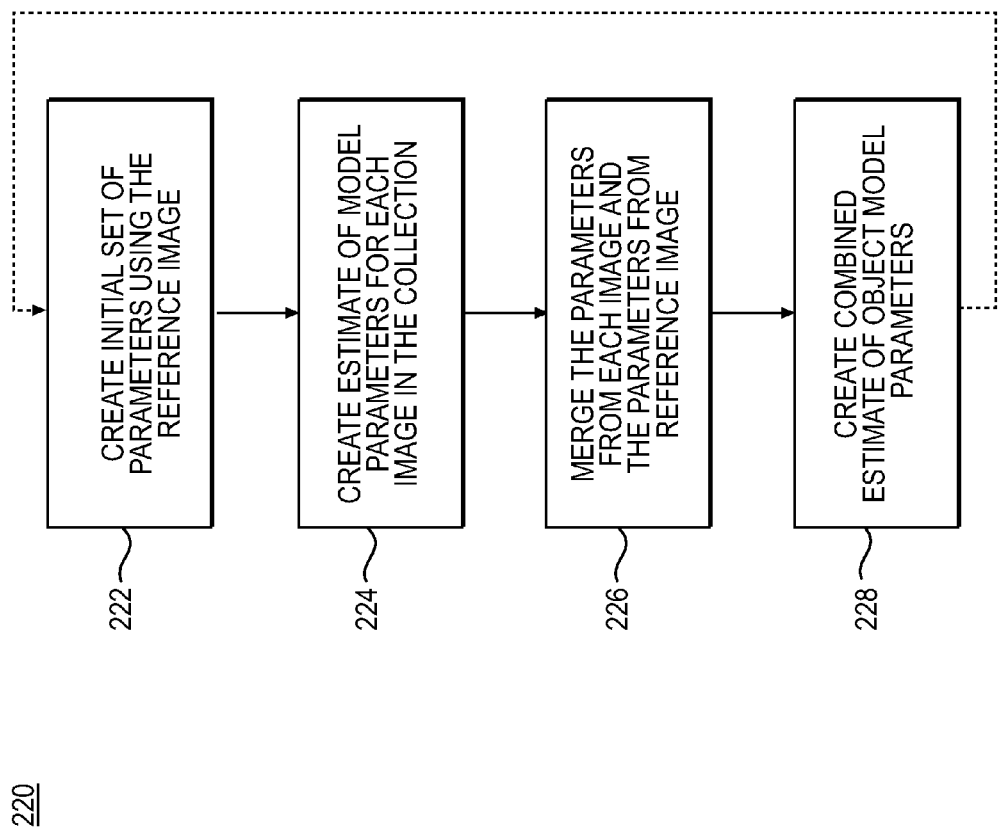
FIG. 2B is a block diagram of an exemplary method for processing various images and/or sets of images to produce final object parameters, according to an exemplary embodiment of the present disclosure.

Reference will now be made in detail to the exemplary embodiments of the invention, examples of which are illustrated in the accompanying drawings. Wherever possible, the same reference numbers will be used throughout the drawings to refer to the same or like parts.

As described above, a new generation of noninvasive tests have been developed that is based on modeling anatomy. Thus, a need exists for accurate modeling. Specifically, there is a need for accurately modeling coronary anatomy to assess patient anatomy, myocardial perfusion, and coronary artery flow. Such a method and system may benefit cardiologists who diagnose and plan treatments for patients with suspected coronary artery disease.

However, because image-based models generated from single images may be insufficient, a need exists for a method for modeling anatomy that may integrate imaging data from multiple sources. For example, compiling multiple images to produce a model may enhance complimentary information in each of the multiple images and reduce imaging artifact in various images. Furthermore, images from multiple imaging modalities may be compiled to create more accurate models and models that take advantage of the imaging strengths unique to each imaging technique. For instance, CT and MR images are sometimes considered complimentary. Creating a model by integrating CT and MR images means that a user no longer has to choose between the benefits of CT imaging versus the benefits of MR imaging in analyzing anatomical data. As an exemplary embodiment, a method for modeling coronary anatomy is described in order to noninvasively assess coronary anatomy, myocardial perfusion, and coronary artery flow. However, such a method and system may be suitable for any anatomy of interest. By extension, reinforcing the advantages of each imaging technique by integrating multiple images may also reduce the impact of disadvantages (e.g., imaging artifacts) associated with various imaging techniques.

Thus, the present disclosure is directed to a new approach of using multiple images in order to create and provide an accurate anatomical model. The extraction of an anatomical model from an image is a common problem in biomedical imaging. Anatomical models may be extracted to measure properties of patient anatomy (e.g., tumor or cardiac volume) or to support biophysical simulation (e.g., fluid simulation, biomechanical simulation, electrophysiological simulation, etc.). In order to accurately measure anatomical properties or predict physiological phenomena via simulation, a precise, patient-specific model must be created of the target anatomy. The present disclosure involves the use of multiple images to achieve a patient-specific anatomical model. For example, the present disclosure may take advantage of complementary information in each of the multiple images or a reduction in different types of imaging artifact in the different images. Although it is possible to construct patient-specific models from geometry derived from a single image, use of multiple images produces a hyper-precise patient-specific anatomical model.

The present disclosure is directed to integrating imaging data from multiple sources to create a single, precise geometric model. Specifically, the present disclosure may receive various types of images or different portions of a target object. The present disclosure may average respective reference images with multiple patient images to create a single geometric model.

Referring now to the figures, FIG. 1 depicts a block diagram of an exemplary system and network for predicting coronary plaque vulnerability from patient-specific anatomic image data. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

FIG. 2A is a block diagram of an exemplary method 200 for creating a patient-specific model from multiple images, according to an exemplary embodiment of the present disclosure. For example, patient images that are obtained via various imaging techniques or at different points in time may be compiled to create a final model. The final model created may depict different parts of anatomy or various aspects of the anatomy, depending on the input images. Some embodiments of the method may include first obtaining a model of the target anatomy object, to which patient images may be mapped. Other embodiments of the method may further include reference images that may serve as a point of comparison for such mapping. Method 200 may be performed by server systems 106, based on information, images, and data received from physicians 102 and/or third party providers 104 over electronic network 100. The method of FIG. 2A may include receiving a representation of a target object for modeling (step 202). In one embodiment, the representation may be stored on an electronic storage device (e.g., hard drive, RAM, network drive, etc.). The representation may include an object localization model (e.g., a boundary model or volumetric model). The representation may also include, but is not limited to, an appearance model or shape model. In one embodiment, the representation may be determined by a set of parameters estimated from the images. The object localization model may include a resultant object model based on the estimated parameters. For instance, the resultant object model may be comprised of a fully determined set of parameters. An exemplary set of parameters to determine an object model is the assignment of a binary indicator value to every pixel, the assignment of a probability or level set value to every pixel. Another set of parameters that may be used to represent an object model is a set of 3D coordinates and triangles to represent the triangulated surface of a 3D object.

Step 204 of method 200 may involve receiving a reference image that depicts the target object. For example, the reference image may be 2-D, 3-D, or 4-D, and the image may be stored in an electronic storage device. In one case, the reference image may be directly associated with the target object. In another case, the reference image may be selected based on inferences from the resultant object model.

Then, step 206 may involve receiving a collection of two or more 2-D, 3-D, or 4-D images that depict at least part of the target object. For instance, this collection of images may be specific to the patient. In one case, the images are stored and/or transferred via an electronic storage device. As used herein, the term, "image," refers to an image regardless of dimension. In addition, each element making up the image may be referred to as a "pixel" or "voxel," regardless of the image size or resolution. For example, each element of a 2-D image may be a pixel, regardless of the image dimensions. Analogously, each element of a 3-D image or volumetric model may be regarded as a "voxel," for images or models of any size or resolution. Step 208 of method 200 may include processing the representation from step 202, the reference image from step 204, and image collection of step 206 to output final object model parameters. For example, step 208 may include outputting the parameters to an electronic storage device and/or performing the processing using a computational device (including but not limited to a computer, laptop, DSP, cloud server, tablet, smart phone, etc.). In one embodiment, method 220 of FIG. 2B may be an exemplary method for performing the processing of step 208. In other words, method 200 may employ method 220 to process gathered information and produce the final object parameters output in step 208.

FIG. 2B is a block diagram of an exemplary method 220 for processing various images and/or sets of images to produce final object parameters, according to an exemplary embodiment of the present disclosure. Method 220 may also be performed by server systems 106, based on information, images, and data received from physicians 102 and/or third party providers 104 over electronic network 100. The method of FIG. 2B may include creating an initial set of parameters for the object model using the reference image (step 222). For example, in one embodiment, initial parameters may be determined by using an image segmentation technique. For example, step 222 may include defining a set of parameters of interest for the object model, and then determining the parameters for the reference image. Alternately, step 222 may include determining a set of parameters available from the reference image. Step 222 may further include determining values of each of the parameters. In some cases, this set of parameters may serve as initialized parameters.

Step 224 may include creating an estimate of some of the object model parameters for each image in the collection (received in step 206). The initialized parameters from step 222 may or may not be used to create the estimate. For example, estimates may be made of more object parameters than are included in the set of initialized parameters. Alternately, estimates may be made for only a subset of the initialized parameters or the full set of initialized parameters.

In one embodiment, step 226 may include updating or merging the parameters from each image in the collection with parameters and parameter values estimated from the reference image. In one embodiment, image parameters from a first set of image parameters may be updated based on image parameters obtained from a second set of images. For example, image parameters may be merged by combining and/or averaging corresponding image parameters obtained from multiple sets of images. Updating parameters may include merging, combining, averaging parameters. Furthermore, updating parameters may include, both changes or verification of existing parameters, as well as generating new parameters. By merging the parameters, step 226 may lead to step 228 of creating a combined estimate of the object. In one embodiment, steps 222-228 may be repeated until the object model parameters converge. The object model parameters may converge into final object parameters. These final object parameters may serve as the output at step 208 of method 200, where final object parameters are output to an electronic storage device.

Figure 3B:
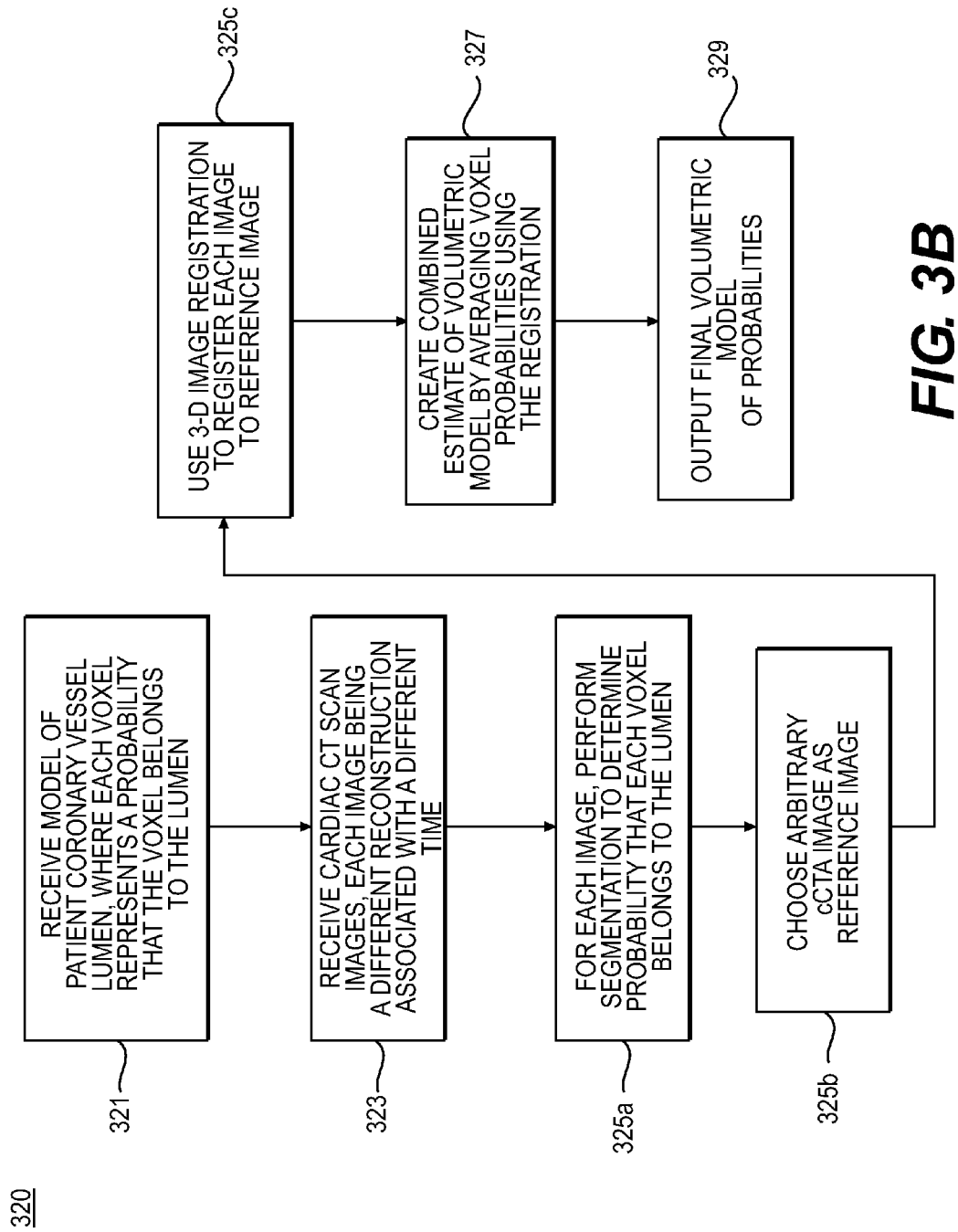
Figure 4A:
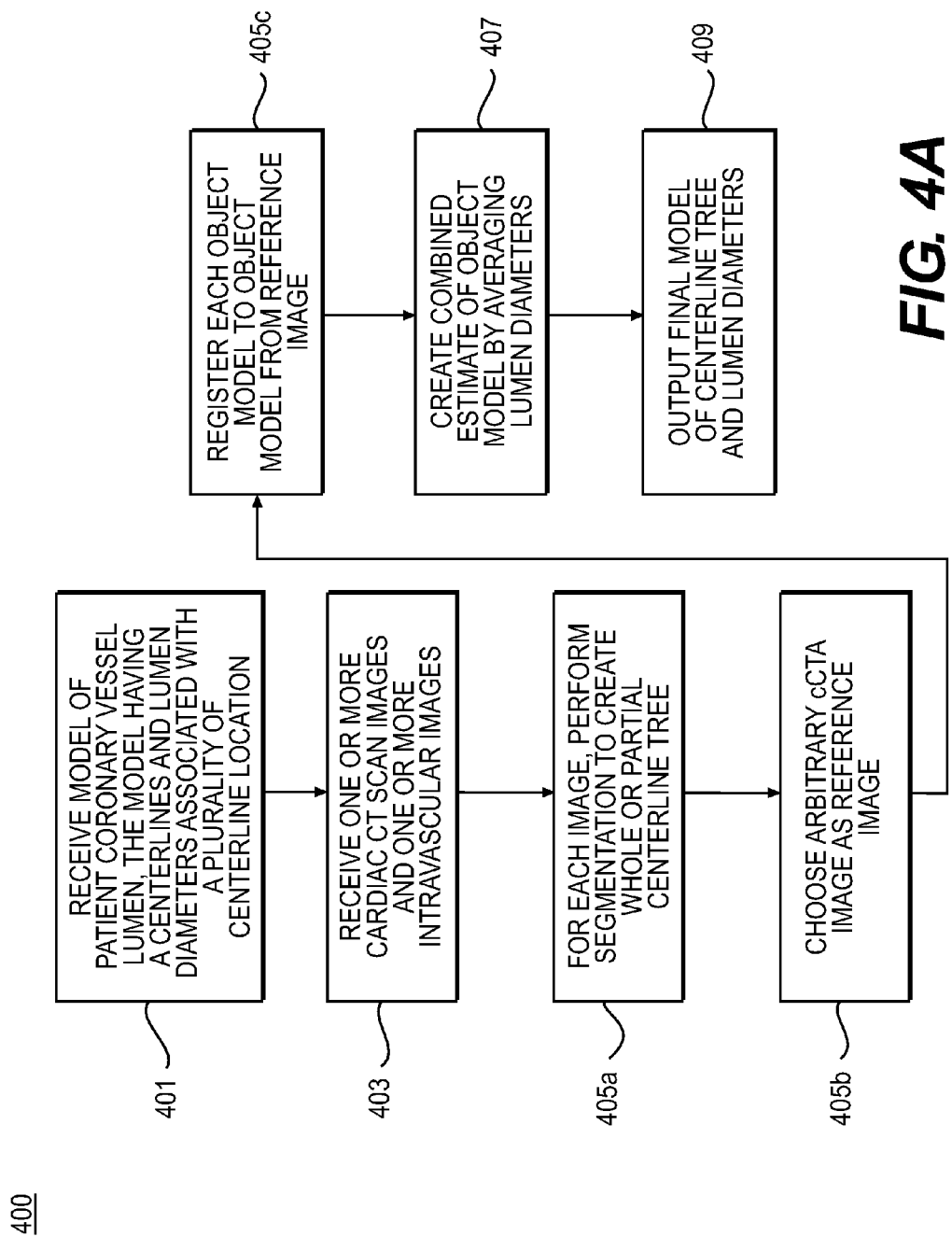
Figure 4B:
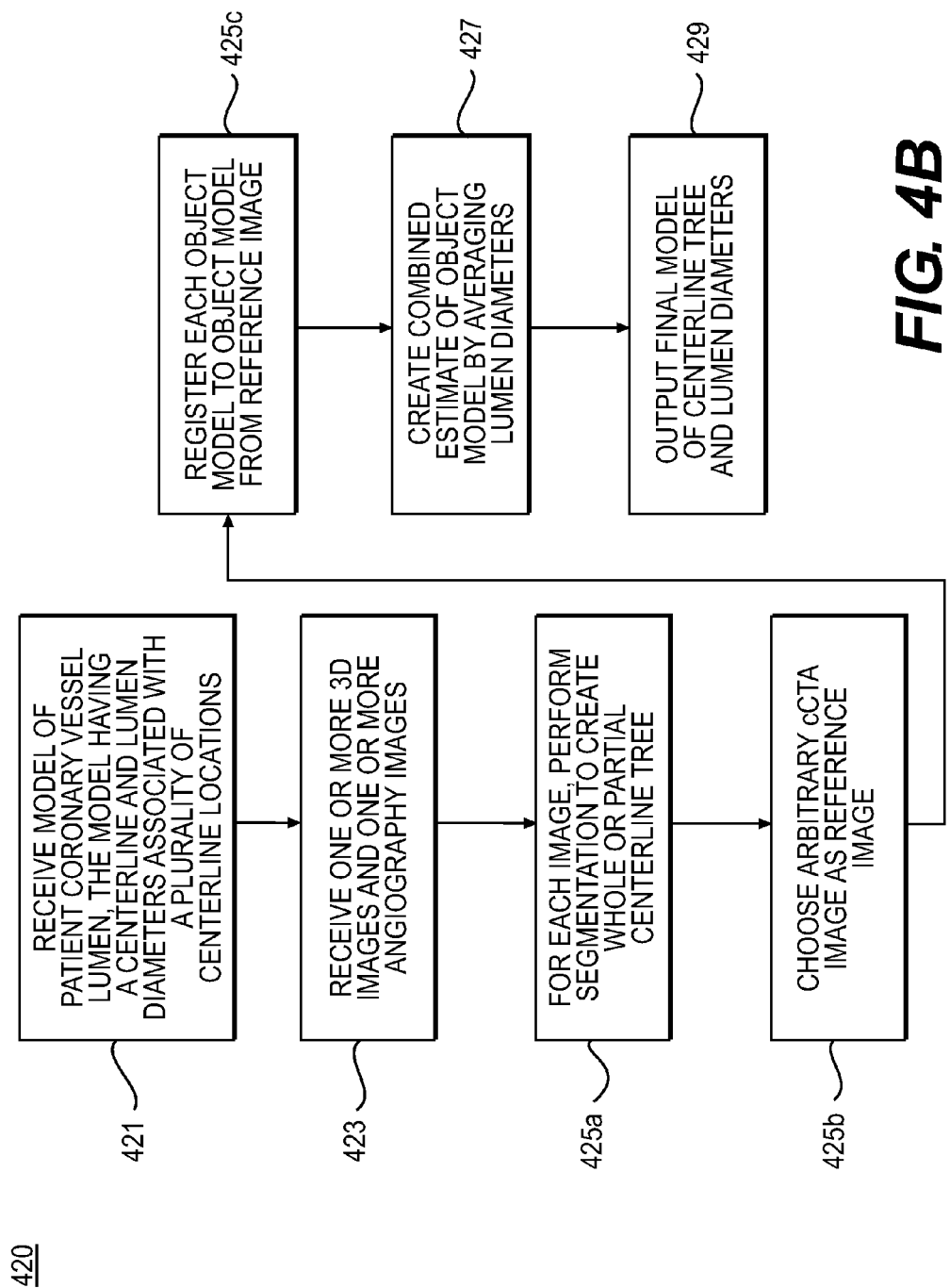
Figure 5:
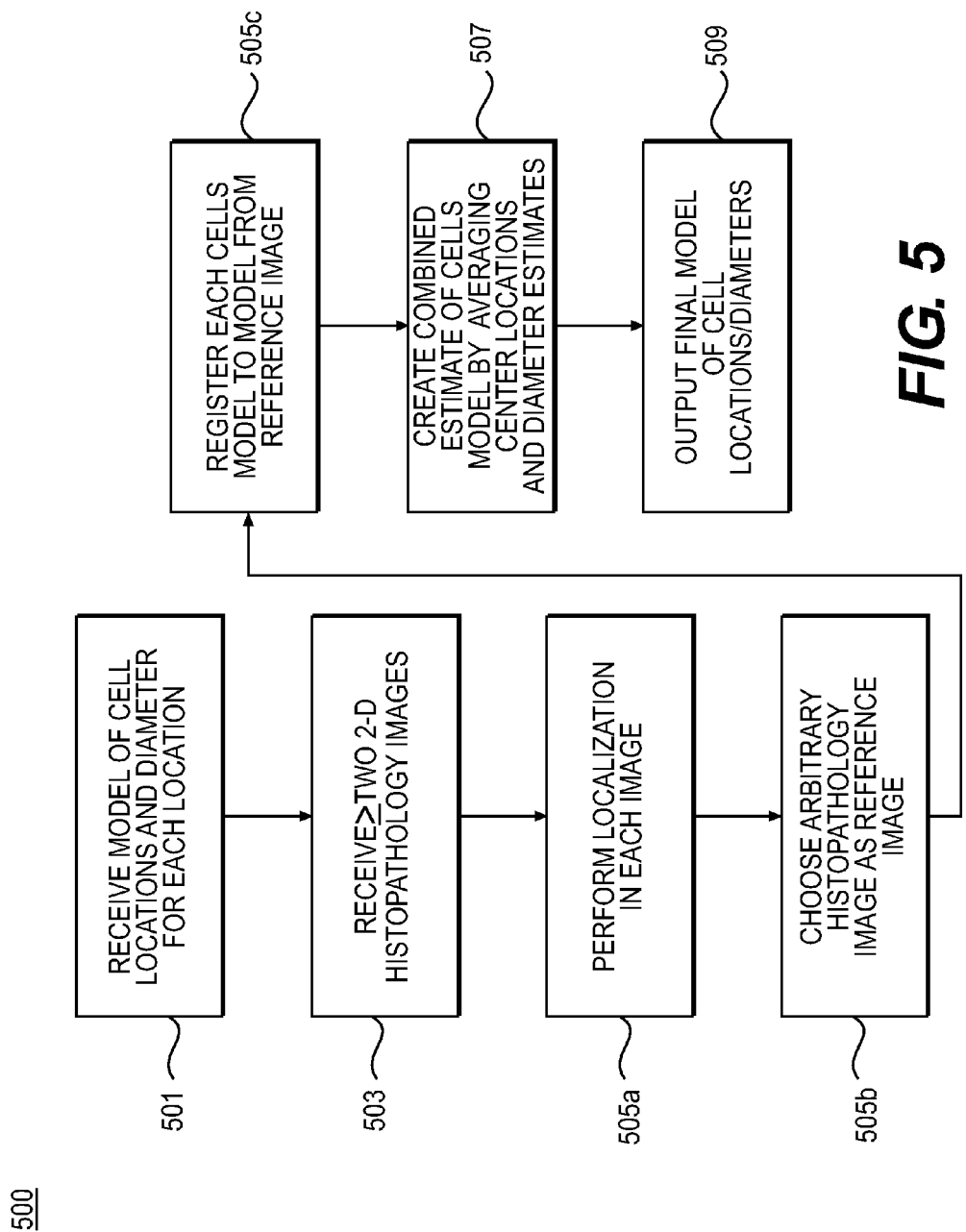
FIG. 5 is a block diagram of an exemplary method for histopathological modeling from multiple optical images, according to an exemplary embodiment of the present disclosure.

Method 200 may be used to produce various models, depending on the patient images used in step 206 and the processing of those images in method 220. The following disclosure presents several exemplary embodiments of, or alternatives to method 200. In general, FIGS. 3A-3C are block diagrams of exemplary methods for obtaining volumetric models of probabilities that given voxels belong to a patient lumen; FIGS. 4A-4C are block diagrams of exemplary methods for producing final object models of patient centerline trees and lumen diameters; and FIG. 5 is a block diagram of an exemplary method to generate a final model of cell locations and diameters. All of the images and final object models discussed may be stored in and/or output to electronic storage devices.

FIGS. 3A-3C depict methods for coronary vessel modeling, where a final volumetric model includes probabilities that each voxel belongs to a patient coronary vessel lumen. For example, different imaging techniques may produce patient images that each portray a coronary vessel lumen in some capacity. Each element (e.g., voxel) of each image may carry some probability that it is part of a vessel. Forming a composite of the images may therefore produce an accurate model of a patient coronary vessel lumen. The model may further include an assessment of the model's accuracy at any point in the model. In general, FIG. 3A is an exemplary method of estimating the probabilities using CTA reconstructions; FIG. 3B is an exemplary method of modeling using cardiac CTA images at different points in time; and FIG. 3C models the coronary vessel from one or more cardiac CTA images and a MR images.

FIG. 3A is a block diagram of an exemplary method 300 for obtaining volumetric models of probabilities based on CTA reconstructions. In one embodiment, coronary vessels may be segmented using multiple cCTA images that represent multiple reconstructions. First, a parameterized representation of a target object may be received and stored on an electric storage device (e.g., hard drive, RAM, network drive, etc.) (step 301). The target object for this instance may be the coronary vessel lumen. For example, the representation for step 301 may be a volumetric model of a patient's coronary vessel lumen, where each voxel represents the probability that the voxel belongs to the patient's coronary vessel lumen. Probabilities may or may not be displayed. For example, in one embodiment, probabilities may be displayed by showing respective probabilities of each voxel belonging to the patient's coronary vessel lumen by displaying a high probability as a high image intensity and a low probability as a low image intensity.

Step 303 may involve receiving multiple 3-D images from a cardiac CT scanner, where each image represents different reconstructions of the cCTA image for the patient. Reconstructions may include, for example, images with different kernels for filtered backprojection and/or iterative reconstruction methods. Employing multiple reconstructions is useful in that each image reconstruction technique has different advantages and disadvantages for different types of image features. Each image reconstruction technique may be better for some types of image features and worse at others (e.g., blooming, streaking, noise, etc.). Using the best aspects of each reconstruction may help achieve a more precise object geometry.

Step 305 may involve determining the probability that each voxel belongs to the patient's coronary vessel lumen. For example, the probability may be determined by performing a segmentation of the coronary vessel lumen in each image. For example, any known technique for performing segmentation to obtain voxel probabilities may be used, such as random walker algorithms or machine learning algorithms that map voxel intensities and their neighbors to probabilities. The segmentation may be performed using any existing technique, and the segmentation may be performed for the coronary vessel lumen independently with respect to each image. For example, segmentation may be performed automatically by a computer system either based on user inputs or without user inputs. For instance, in an exemplary embodiment, the user may provide inputs to the computer system in order to generate a first initial model. For another example, the computer system may display to the user a 3-D image or slices thereof produced from the CCTA data. The 3-D image may include portions of varying intensity of lightness. For example, lighter areas may indicate the lumens of the aorta, the main coronary arteries, and/or the branches. Darker areas may indicate the myocardium and other tissue of the patient's heart.

Step 307 may involve averaging the probabilities (from step 305) across the images to create a combined estimate of the volumetric model of the probability of each voxel belonging to the patient lumen. In one embodiment, steps 305 and 307 may be performed using a computer. Finally, the final, averaged volumetric model of the probabilities may be output (step 309), for example, to an electronic storage device. For example, the averaged volumetric model of the probabilities may be output in the form of a color overlay showing the boundary of a level set on the probabilities, or as a set of raw probabilities.

FIG. 3B is a block diagram of an exemplary method 320 for obtaining volumetric models of probabilities based on CTA images obtained at different points in time. As in method 320, step 321 involves obtaining a parameterized representation of a target object (e.g., a coronary vessel lumen). The representation may be a volumetric model of a patient's coronary vessel lumen in which each voxel represents the probability that the voxel belongs to the patient's coronary vessel lumen. Similar to step 303, step 323 may involve receiving multiple 3-D images from a cardiac CT scanner where each image represents a different reconstruction of the cCTA image for a patient. Unique to method 320, the images may represent acquisitions from a single patient, at multiple points in time (e.g., time points within the cardiac cycle or an initial acquisition and follow-up scan). Using images at multiple time points means that each image may contain independent information that may contain less artifact or better quality in different regions of the image. Method 320 may include using the best aspects of each reconstruction to achieve a final model of precise object geometry. The images for step 323 may be stored in an electronic storage device. For example, a storage device may determine a new image acquisition and update a final volumetric model by taking into account the new acquisition.

Step 325a may reflect step 305 in determining the probability that each voxel belongs to the patient's coronary vessel lumen. For example, step 325a may include finding the probability by performing a segmentation of the coronary vessel lumen independently in each image (using any existing technique). Next, step 325b may involve choosing a reference image. For example, the reference image may be arbitrary among the acquired images, retrieved from a reference image repository, selected intentionally from a set of acquired images, etc. Then, 3-D registration may be used to register each image to the reference image (step 325c). In certain embodiments, steps 325a-325c may be analogous to steps 345a-345c of FIG. 3C.

Step 327, like step 307, may involve creating a combined estimate of the volumetric model by averaging probabilities across images. However, the images for step 327 may include patient images and the reference image. The image registration may be used to map each voxel to another voxel, meaning mapping a location in each image to a location (or locations) in the reference image and/or other images. The mapping may be performed using any method such that voxels in two images may be identified as being representations of the same part of the target object (e.g., coronary vessel lumen). Since the voxels correspond to the same part, the voxel probabilities may be combined. Therefore, averaging the probability of each voxel belonging to the patient lumen may create a merged, averaged voxel probability for each voxel. Finally, step 329 may include outputting the final volumetric model of the probabilities to an electronic storage device.

FIG. 3C is a block diagram of an exemplary method 340 for obtaining volumetric models of probabilities based on a plurality of cCTA images that represent the coronary tree and a plurality of cardiac magnetic resonance (MR) images that also depict the coronary tree. Step 341 involves receiving a parameterized representation of a coronary vessel lumen stored on an electronic storage device, similar to steps 301 and 321. Again, the representation may be a volumetric model of the patient's coronary vessel lumen, in which each voxel represents the probability that the voxel belongs to the patient's coronary vessel lumen. At step 343, in addition to receiving one or more 3-D images from a cardiac CT scan, step 343 may further include receiving one or more 3-D images from a cardiac MR scan of a patient. Both CT and MR cardiac images may be acquired to obtain different cardiac information available from each modality (e.g., fine detail with CT and viability with MR). Further, MR imaging may exhibit fewer blooming artifacts near calcium than CT images exhibit, so MR images may be more useful in some cases for examining the geometry of calcified lesions. Both the CT scan(s) and MR scan(s) may be stored in an electronic storage device.

As previously stated, steps 345a-345c may be similar to steps 325a-325c, as applied to a context involving MR images. These steps may all be performed using a computer. Step 345a, like steps 305 and 325a, may involve segmentation that determines probability associated with each voxel that the voxel belongs to the patient's coronary vessel lumen. Then, step 345*b* may involve choosing an arbitrary image or an image with the greatest spatial resolution as a reference image. Thus, the reference image may, in some cases, have the smallest voxel size. Step 345*c* may involve using 3-D image registration to register each image to the reference image from step 345*b*. For example, step 345*c* may include using 3-D image registration to register each voxel probability in each image to each respective voxel probability in the reference image. Steps 345*c* and 347 may involve creating a combined estimate of a volumetric model by using the image registration to map each voxel probability to a corresponding voxel probability of the reference image. Again, in one embodiment, the mapping may create a merged (e.g., averaged) voxel probability. Step 349, analogous to steps 309 and 329, may involve outputting the averaged, final volumetric model of the probabilities to an electronic storage device.

FIGS. 4A-4C depict methods for coronary vessel modeling, where the final model may be an object model of the centerline tree and lumen diameters of the coronary vessel. FIG. 4A represents vessel modeling from a cardiac CTA image and an intravascular ultrasound (IVUS) and/or intravascular optical coherence tomography (OCT) image, while FIGS. 4B and 4C are two embodiments of a method of coronary vessel modeling from a cardiac CTA image and an angiography image.

FIG. 4A is a block diagram of an exemplary method 400 for coronary vessel modeling from a cardiac CTA image and an IVUS/OCT image. For example, a parameterized representation of the target object (e.g., a coronary vessel lumen) may be obtained (step 401). The representation may be a model of a patient's coronary vessel lumen in which each vessel is represented by a centerline and the lumen boundary is represented by a lumen diameter associated with each centerline location.

Step 403 may involve receiving one or more 3-D images from a cardiac CT scan and one or more intravascular images of the same patient. For example, the coronary vessels may be segmented using one or more cCTA images that represent the entire coronary tree and one or more IVUS or OCT images of at least a portion of the coronary tree. Going forward, the term, "intravascular images," may be taken to refer to the IVUS and/or OCT images. Cardiac CTA and intravascular cardiac images may be acquired due to different cardiac information generated by each modality (e.g., complete 3-D vessel tree from CT and high-resolution vessel geometry from intravascular imagery). Furthermore, intravascular imaging may exhibit fewer blooming artifacts near calcium than are exhibited by CT. As a result, intravascular imaging may be especially useful for the purpose of examining the geometry of calcified lesions.

For step 405*a*, a segmentation of the coronary vessel lumen may be performed independently in each image to create either a complete centerline tree (e.g., for the coronary CT images) or a part of the centerline tree (e.g., for intravascular images). This segmentation may determine the diameter of the coronary vessel lumen at each location of the centerline. Step 405*b* may involve choosing an arbitrary cCTA image as the reference image, and step 405*c* may involve using registration to register each object model or part of an object model to the object model obtained from the reference image. Again, each object model may be comprised of one or more centerlines and/or one or more lumen diameters. For step 407, a combined estimate of the object model may be created by averaging the lumen diameter at each centerline location with an estimate from each source (e.g., as determined from step 405*a*). All the steps of method 400 may be performed using a computer, especially steps 405*a*-407. Lastly, a final, averaged object model of the centerline tree and lumen diameters may be output (step 409).

FIG. 4B is a block diagram of an exemplary method 420 for coronary vessel modeling from a cardiac CTA image and an angiography image. In one embodiment, step 421 may include receiving a parameterized representation of a coronary vessel lumen as a target object, where the representation may be a model of the lumen. For example, each vessel may be represented by a centerline and the lumen boundary may be represented by a lumen diameter associated with each centerline location. Step 423 may involve receiving one or more 3-D images from a cardiac CT scan and one or more angiography images of the same patient. Again, coronary vessels may be segmented using one or more cCTA images that represent the entire coronary tree, but in contrast to method 400, at least a portion of the coronary tree may be segmented using one or more 2-D angiography images, rather than (or in addition to) IVUS and/or OCT images. Cardiac CTA and angiography images may be acquired due to different cardiac information generated by each modality (e.g., complete 3-D vessel tree from CT and high-resolution vessel geometry from the angiography). Furthermore, angiography imaging may exhibit fewer blooming artifacts near calcium than exhibited by CT, making it useful for examining the geometry of calcified lesions.

In certain embodiments, steps 425*a*-425*c* may be analogous to steps 445*a*-445*c* of FIG. 4C; and steps 425*a*-427 and steps 445*a*-447 may all be performed using a computer. Step 425*a* may involve performing segmentation of the coronary vessel lumen independently in each image to create a complete centerline tree (e.g., for the coronary CT images) or a part of the centerline tree (e.g., for the angiography images). The segmentation may determine the diameter of the coronary vessel lumen at each point of the centerline. Then, an arbitrary cCTA image may be chosen as a reference image (step 425*b*) and registration may be used to register each object model or part of an object model to the object model obtained from the reference image. Each object model may be comprised of one or more centerline(s) and one or more lumen diameter(s). If viewing angles are available for the angiography images, the information from that analysis may be taken into account when registering the models (step 425*c*). Step 427 may involve creating a combined estimate of the object model by averaging lumen diameter(s) at each centerline location with an estimate of the diameter from each source (e.g., as given by step 425*a*). Step 429 may include outputting a final, averaged object model of centerline tree and lumen diameters.

FIG. 4C is a block diagram of an exemplary method 440, also for coronary vessel modeling from a cardiac CTA image and an angiography image. Method 440 may be used as an alternative to method 420. Like method 420, method 440 may begin with obtaining a parameterized representation that is a model of a patient's coronary vessel lumen, in which each lumen is represented by a centerline, and the lumen boundary may be represented by a lumen diameter associated with each centerline location (step 441). Step 443*a* may involve receiving a 3-D image from a cardiac CT scan and one or more angiography images of the same patient with viewing angles for each angiography image. A further step 443*b* may involve receiving additional patient—specific information, such as, for example, an upper and/or lower bound on total vascular volume. Step 445*a*, like step 425*a*, may include performing a segmentation of the coronary vessel lumen to create a complete centerline tree (e.g., for the coronary CT images) or part of the centerline tree (e.g., for the angiography images), where the segmentation may determine the diameter of the coronary vessel lumen at each location of the centerline. In contrast to the arbitrarily designated reference images from step 425*b*, step 445*b* may choose the cCTA image as the reference image. Then, step 445*c* may involve evaluating whether all the 2-D projections of the geometric model onto the 2-D angiography spaces match respective 2-D segmentations and constraints of the additional patient-specific information. In one embodiment, the matching may be done in a Bayesian framework if the projections are described as probability density functions. If a match is achieved, a geometric representation may be extracted from the cCTA image (step 447). Step 449 may include outputting a final object model of the centerline tree and lumen diameters.

FIG. 5 is a block diagram of an exemplary method 500 for modeling anatomy from multiple optical (e.g., histopathological) images. For example, optical images may be obtained for various types of tissue. Tissue samples may be from surgery, biopsy, or autopsy. Histopathological examination of tissue samples may include processing multiple optical images of the tissue in order to create a final model of cells of the tissue sample. Such information may offer insight into diseases affecting the tissue. The method may begin with obtaining a parameterized representation of target objects (step 501). In one embodiment, the target objects may be a set of cell locations in a tissue sample. For example, step 501 may include retrieving a model of cell locations and a diameter for each location. Step 503 may involve receiving two or more 2-D or 3-D histopathology images of the same tissue sample. Cell locations of a tissue sample may be computed from multiple 2-D histopathology optical images. Multiple images might be acquired to provide a hyper-precise localization of all cells in the tissue sample. Step 505*a* may then include performing a localization of all cells in an image to create a center location and diameter estimate for each cell. Then, an arbitrary histopathology image may be chosen as the reference image (step 505*b*), and registration may be used to register each cells model to the cells model obtained from the reference image (step 505*c*). In one case, each cells model may comprise a center location and/or diameter for each cell in a field of view associated with the tissue sample. Then, step 507 may include averaging center locations and diameter estimates for each cell from all cell models. Based on the averaging, step 507 may further involve creating a combined estimate of the cells model. Again, an output of the final, averaged model of cell locations and/or diameters may be made (step 509).

Thus, modeling may be improved using multiple images, whether the variations are images acquired from reconstructions, various imaging modalities, or acquisitions at different points in time. Creating models by aggregating multiple images permits the combination of benefits of different imaging modalities models, reduces errors or imperfections in individual image acquisitions, and strengthens the credibility of the final model. The technique of modeling using multiple images may be applied to model any target object, anatomy of interest, or information associated with that target object and/or anatomy or interest.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of modeling at least a portion of a patient's vasculature, using a computer system, the method comprising:
  receiving one or more three-dimensional images of a portion of a patient's coronary vasculature;
  receiving one or more two-dimensional images that are generated independently from the one or more three-dimensional images, wherein the one or more two-dimensional images include images of the portion of the patient's coronary vasculature;
  determining, from the one or more three-dimensional images, one or more three-dimensional image based anatomical parameters of the portion of the patient's coronary vasculature;
  determining, from the independently-generated one or more two-dimensional images, one or more two-dimensional image based anatomical parameters of the portion of the patient's coronary vasculature;
  updating the one or more three-dimensional image based anatomical parameters based at least on the one or more two-dimensional image based anatomical parameters; and
  generating a model of at least the portion of the patient's coronary vasculature based on the updated three-dimensional image based anatomical parameters.

2. The method of claim 1, wherein the one or more three-dimensional images include one or more cardiac computed tomography images and the one or more two-dimensional images include one or more intravascular images.

3. The method of claim 1, wherein the one or more three-dimensional images include one or more cardiac computed tomography images and the one or more two-dimensional images include one or more angiography images.

4. The method of claim 1, further including:
  obtaining an initial model of at least the portion of the patient's coronary vasculature, wherein the generated model is based on the initial model.

5. The method of claim 1, further comprising:
  performing a segmentation of at least one of the one or more three-dimensional images of the portion of the patient's coronary vasculature; and
  determining, using the segmentation of the at least one of the one or more three-dimensional images, one or more segmentation-based anatomical parameters of the portion of the patient's coronary vasculature as the one or more three-dimensional image based anatomical parameters.

6. The method of claim 1, further comprising designating one of the three-dimensional or two-dimensional images as a reference image, wherein updating the one or more three-dimensional image based anatomical parameters based at least on the one or more two-dimensional image based anatomical parameters comprises:
  generating an object model of a centerline and lumen diameters from each of the one or more three-dimensional image based or two-dimensional image based anatomical parameters;
  registering each object model of a centerline and lumen diameters from each of the one or more three-dimensional image based or two-dimensional image based anatomical parameters to an object model associated with the reference image; and
  averaging one or more lumen diameters of each object model with one or more lumen diameters of the object model associated with the reference image.

7. The method of claim 1, wherein the model of the patient's coronary vasculature includes the updated three-dimensional image based anatomical parameters for a centerline tree and one or more lumen diameters at locations along the centerline tree.

8. The method of claim 1, further including:
designating one of the three-dimensional images as a reference image;
extracting a geometric representation from the reference image; and
generating the model of the patient's coronary vasculature based on the geometric representation.

9. The method of claim 1, further including:
receiving patient-specific information, including upper and/or lower bound information on total vascular volume; and
generating the model of the patient's coronary vasculature further based on the received patient-specific information.

10. A system of modeling at least a portion of a patient's anatomy, using a computer system, the system comprising:
a data storage device storing instructions for modeling based on patient-specific anatomic image data; and
a processor configured to execute the instructions to perform a method including:
receiving one or more three-dimensional images of a portion of a patient's coronary vasculature;
receiving one or more two-dimensional images that are generated independently from the one or more three-dimensional images, wherein the one or more two-dimensional images include images of the portion of the patient's coronary vasculature;
determining, from the one or more three-dimensional images, one or more three-dimensional image based anatomical parameters of the portion of the patient's coronary vasculature;
determining, from the independently-generated one or more two-dimensional images, one or more two-dimensional image based anatomical parameters of the portion of the patient's coronary vasculature;
updating the one or more three-dimensional image based anatomical parameters based at least on the one or more two-dimensional image based anatomical parameters; and
generating a model of at least the portion of the patient's coronary vasculature based on the updated three-dimensional image based anatomical parameters.

11. The system of claim 10, wherein the one or more three-dimensional images include one or more cardiac computed tomography images and the one or more two-dimensional images include one or more intravascular images.

12. The system of claim 10, wherein the one or more three-dimensional images include one or more cardiac computed tomography images and the one or more second images include one or more angiography images.

13. The system of claim 10, wherein the processor is further configured for:
obtaining an initial model of at least the portion of the patient's coronary vasculature, wherein the generated model is based on the initial model.

14. The system of claim 10, further comprising:
performing a segmentation of at least one of the one or more three-dimensional images of the portion of the patient's coronary vasculature; and
determining, using the segmentation of the at least one of the one or more three-dimensional images, one or more segmentation-based anatomical parameters of the portion of the patient's coronary vasculature as the one or more three-dimensional image based anatomical parameters.

15. The system of claim 10, wherein the processor is further configured for designating one of the three-dimensional or two-dimensional images as a reference image; wherein updating the one or more three-dimensional image based anatomical parameters based at least on the one or more two-dimensional image based anatomical parameters comprises:
generating an object model of a centerline and lumen diameters from each of the one or more three-dimensional image based or two-dimensional image based anatomical parameters;
registering each object model of a centerline and lumen diameters from each of the one or more three-dimensional image based or two-dimensional image based anatomical parameters to an object model associated with the reference image; and
averaging one or more lumen diameters of each object model with one or more lumen diameters of the object model associated with the reference image.

16. The system of claim 10, wherein the model of the patient's coronary vasculature includes the updated three-dimensional image based anatomical parameters for a centerline tree and one or more lumen diameters at locations along the centerline tree.

17. The system of claim 10, the processor is further configured for:
designating one of the three-dimensional images as a reference image;
extracting a geometric representation from the reference image; and
generating the model of the patient's coronary vasculature based on the geometric representation.

18. The system of claim 10, the processor is further configured for:
receiving patient-specific information, including upper and/or lower bound information on total vascular volume; and
generating the model of the patient's coronary vasculature further based on the received patient-specific information.

19. A non-transitory computer readable medium for use on a computer system containing computer-executable programming instructions for performing a method of modeling at least a portion of a patient's anatomy, the method comprising:
a data storage device storing instructions for modeling based on patient-specific anatomic image data; and
a processor configured to execute the instructions to perform a method including:
receiving one or more three-dimensional images of a portion of a patient's coronary vasculature;
receiving one or more two-dimensional images that are generated independently from the one or more three-dimensional images, wherein the one or more two-dimensional images include images of the portion of the patient's coronary vasculature;
determining, from the one or more three-dimensional images, one or more three-dimensional image based anatomical parameters of the portion of the patient's coronary vasculature;
determining, from the independently-generated one or more two-dimensional images, one or more two-dimensional image based anatomical parameters of the portion of the patient's coronary vasculature;

updating the one or more three-dimensional image based anatomical parameters based at least on the one or more two-dimensional image based anatomical parameters; and generating a model of at least the portion of the patient's coronary vasculature based on the updated three-dimensional image based anatomical parameters.

20. The non-transitory computer readable medium of claim 19, wherein the one or more three-dimensional images include one or more cardiac computed tomography images and the one or more two-dimensional images include one or more intravascular images or one or more angiography images.

21. A computer-implemented method of modeling at least a portion of a patient's vasculature, using a computer system, the method comprising:

receiving one or more three-dimensional images of a portion of a patient's coronary vasculature;

receiving one or more other images that are generated independently from the one or more three-dimensional images, wherein the one or more other images include images of the portion of the patient's coronary vasculature;

determining, from the one or more three-dimensional images, one or more three-dimensional image based anatomical parameters of the portion of the patient's coronary vasculature;

determining, from the independently-generated one or more other images, one or more second anatomical parameters, the second anatomical parameters defining a dimension of patient anatomy in a direction perpendicular to a centerline of the portion of the patient's coronary vasculature from at least one of the one or more independently-generated other images of the patient's coronary vasculature;

updating the one or more three-dimensional image based anatomical parameters based at least on the one or more second anatomical parameters; and generating a model of at least the portion of the patient's coronary vasculature based on the updated three-dimensional image based anatomical parameters.

* * * * *